United States Patent [19]

Cobb

[11] Patent Number: 5,205,408

[45] Date of Patent: Apr. 27, 1993

[54] SYRINGE CASE

[76] Inventor: Neal E. Cobb, 181 Sloan St., Roswell, Ga. 30075

[21] Appl. No.: 834,657

[22] Filed: Feb. 12, 1992

[51] Int. Cl.⁵ .................................................. A65D 85/00
[52] U.S. Cl. ................................... 206/364; 215/220; 604/192; 604/263
[58] Field of Search .................. 206/364-366; 604/192, 263; 215/220, 253

[56] References Cited

U.S. PATENT DOCUMENTS

| | | | |
|---|---|---|---|
| 3,149,717 | 9/1964 | Castelli | 206/365 |
| 3,367,488 | 2/1968 | Hamilton | 206/365 |
| 3,828,775 | 8/1974 | Armel | 206/365 X |
| 3,885,562 | 5/1975 | Lampkin . | |
| 4,527,701 | 7/1985 | Schaubeck | 215/220 |
| 4,555,036 | 11/1985 | Bekkers et al. | 215/220 |
| 4,623,336 | 11/1986 | Pedicano et al. . | |
| 4,629,453 | 12/1986 | Cooper . | |
| 4,659,330 | 4/1987 | Nelson et al. . | |
| 4,669,620 | 6/1987 | Coifman | 215/220 |
| 4,717,386 | 1/1988 | Simmons . | |
| 4,735,617 | 4/1988 | Nelson et al. . | |
| 4,767,412 | 8/1988 | Hymanson . | |
| 4,781,697 | 11/1988 | Slaughter . | |
| 4,801,013 | 1/1989 | Bruno | 206/366 |
| 4,826,488 | 5/1989 | Nelson et al. . | |
| 4,956,907 | 9/1990 | Bruno | 206/366 X |
| 4,985,020 | 1/1991 | Kasuya . | |
| 5,054,633 | 10/1991 | Reijenga | 215/220 |
| 5,067,949 | 11/1991 | Freundlich et al. | 604/263 |

Primary Examiner—Bryon P. Gehman
Attorney, Agent, or Firm—Kennedy & Kennedy

[57] ABSTRACT

A case (10) for housing a syringe (40) and for use in removing and replacing a protective sheath (45) covering the syringe needle (44). The case has a removable end cap (11) mounted to a tubular member (12) and an aperture (31) sized and shaped to receive the sheath. The cap has a post (24) movably mounted therein for movement to indicate the removal and replacement of the cap.

7 Claims, 1 Drawing Sheet

U.S. Patent    Apr. 27, 1993    5,205,408
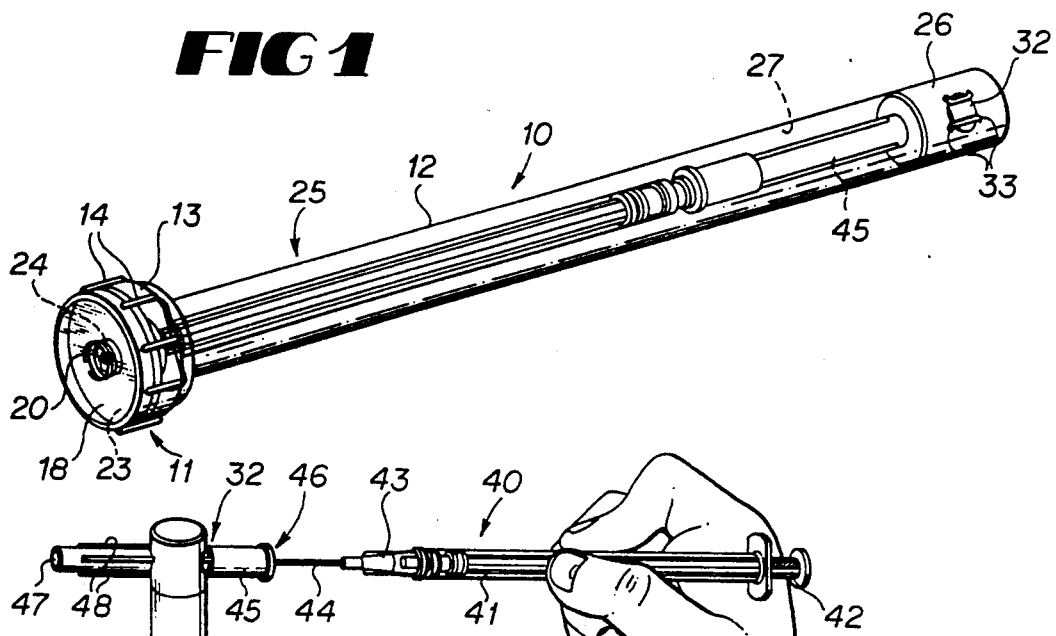
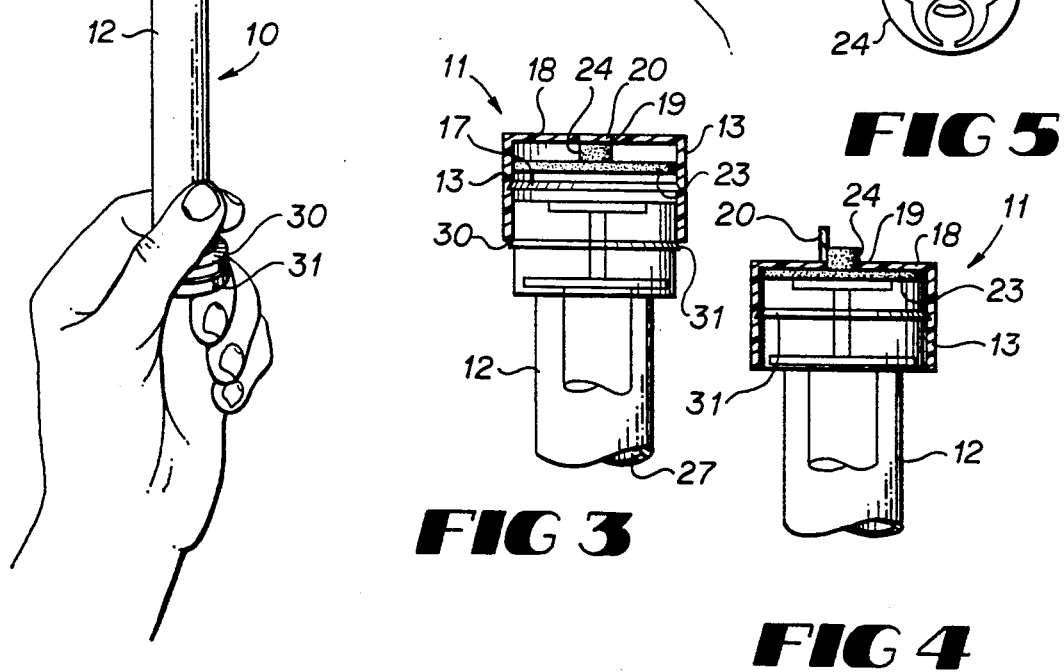

SYRINGE CASE

TECHNICAL FIELD

This invention relates to cases for housing syringes.

BACKGROUND OF THE INVENTION

Disposable hypodermic syringes are widely used in hospitals and other medical facilities to draw body fluids from and to inject medications into patients. These syringes are made disposable because of the difficulties and inefficiencies involved in re-sterilizing syringes for reuse. Because these syringes are intended to be disposed of after use, a problem arises as to their safe post-use storage and disposal and in preventing them from being accidentally reused.

Typically, these syringes are provided with a removable, protective sheath covering the syringe needle. These sheaths are removed before use and often replaced after use for their safe disposal or storage for subsequent medical procedures. For example, once blood has been drawn into a syringe and the syringe extracted from the patient, the needle tip is commonly capped and then placed in ice pending subsequent laboratory examination and analysis of the blood sample. In doing this the protective sheath has commonly been placed over the needle with one hand while holding the syringe with the other hand. This method has been hazardous due to the fact that syringe users sometimes prick or inject themselves by accident when trying to align and insertion the needle into its sheath. Where such occurs there is a possibility that a disease may be transmitted from the patient to the nurse or other medical personnel using the syringe.

Additionally, once a syringe is used it is often impossible to distinguish it from unused, sterile syringes. For this reason immediate disposal of the syringe is recommended. However, due to the possible inaccessibility of proper disposal containers for hazardous medical waste, this may not always be possible. Therefore, accidental reuse of contaminated syringes may occur.

It thus is seen that a need remains for a syringe case with which syringes may be more safely unsheathed, resheathed and stored. It is to the provision of such therefore that the present invention is primarily directed.

SUMMARY OF THE INVENTION

In a preferred form of the invention a case is provided for housing a syringe having a needle, a hub from which the needle extends, a barrel coupled with the hub and a removable protective sheath covering the needle. The case comprises an elongated tubular member having an open end and an aperture located adjacent another end. The aperture has a size and shape to hold the syringe protective sheath. The case further comprises a cap having a passage therethrough for capping the open end of the tubular member and indicator means for indicating that the cap has been removed and replaced upon the tubular member. The indicator means includes a post mounted adjacent the tubular member open end positioned to extend through the cap passage upon the cap being replaced on the tubular member. With this construction, the protective sheath may be removed and replaced over the needle by positioning the sheath within the aperture without movement of the exposed needle towards a user's hand.

BRIEF DESCRIPTION OF THE DRAWING

FIG. 1 is a perspective view of a syringe case that embodies principles of the invention is a preferred form shown with a syringe housed therein.

FIG. 2 is a side view of the case of FIG. 1 shown being used to unsheath and resheath a syringe needle.

FIG. 3 is a cross-sectional view of a cap portion of the syringe case of FIG. 1 in a pre-use condition.

FIG. 4 is a cross-sectional view of a cap portion of the syringe case of FIG. 1 in a post-use condition.

FIG. 5 is a top view of the indicator post member of the syringe case of FIG. 1.

DETAILED DESCRIPTION

With reference next to the drawing, there is shown a syringe case 10 having an cup-shaped end cap 11 and an elongated, tubular member 12 both of which are preferably made of a transparent plastic material. The end cap 11 has a generally cylindrical side wall 13 with a series of exterior knurls 14 or ribs and an interior annular indentation 17. The end cap also has a flat end wall 18 with a centrally located passage 19 therethrough which may be closed and opened by a hinged flap 20. A movable, disk-shaped plate 23 having a post 24 extending centrally therefrom is telescopically mounted within the end cap. The post 24 is sized and shaped to extend through the cap passage 19 to ambiance. As best shown in FIG. 5, the top of the post may be provided with a hazardous waste symbol 34 for quick hazardous waste recognition.

The tubular member 12 has a hollow portion 25 with an elongated, cylindrical channel 27 therethrough and an integrally formed solid portion 26 at one end. The other end of the hollow portion 25 is open and is formed with an enlarged, annular rim 30 that has a peripheral, annular ridge 31. The solid portion 26 of the tubular member has an aperture 32 extending therethrough oriented normal to the cylindrical channel 27. The aperture 32 is generally cylindrical except for four, angularly spaced, elongated grooves 33.

In FIGS. 1 and 2 a conventional syringe 40 is shown which has a hollow, cylindrical barrel 41 formed with an opening at one end through which an end of a plunger 42 extends. A hub 43 extends from the other end of the barrel to which a hypodermic needle 44 is mounted. The needle is coverable by a removable, protective sheath 45 that has an open end 46 and a closed end 47. The exterior of the sheath has four, angularly spaced, parallel ridges 48 which provide the sheath with a size and shape to be snugly received in the case aperture 32. Since protective sheaths are usually slightly tapered, the aperture 32 may also be slightly tapered to provide a close fit. The taper of the aperture also allows for a range of sheath sizes to be accommodated.

The syringe 40 may be initially stored in the case channel 27 with the end cap 11 press fitted on the case rim 30 and with the cap passage 19 closed by the hinged flap 20. An operator such as a nurse, nurse's aid or hospital attendant, may remove the syringe from the case by removing the end cap so as to allow the syringe to be accessed and removed. As shown in FIG. 2, once the syringe is removed from the case it may be grasped with one of the operator's hands and the case grasped with the other of the operator's hands near its open end 28. The syringe protective sheath is then guided into the aperture 32 and snugly mounted therein with its elongated ridges 48 engaging the elongated grooves 33 about the aperture. The syringe is then withdrawn from the protective sheath.

To facilitate sheath removal the case may be rotated about its longitudinal axis against the syringe so as to create a crimping or binding force upon the sheath. The syringe may then be loosened from the sheath and withdrawn. Cooperation of the sheath ridges 48 with the aperture grooves 33 bounding the aperture 32 holds the sheath stationary so that the syringe may be twisted while being withdrawn to facilitate unsheathing sheaths that are tightly mounted sheaths. The case may then be set upon a level surface with the sheath still mounted within its aperture 32.

To resheath the syringe needle, the case is again grasped near its open end distally from the sheath 45. The syringe needle is aligned with and then forced into the sheath as shown in FIG. 2. Should the needle be misaligned during resheathing it will pass harmlessly to one side of the sheath at a substantial distance from and thus without pricking the operator's hand holding the case. Indeed, it can be seen that the exposed needle need never be pointed towards or moved towards the operator's hand. Once its needle is resheathed the syringe may be removed from the aperture 32 by jiggling it loose or by pulling the sheath out of the aperture.

After resheathing the syringe may be placed back into the channel 27 of the tubular member and the end cap 11 pushed forcefully onto the flanged rim 30 past its initial position, shown in FIG. 3, to its locked position shown in FIG. 4. During this recapping operation the rim 30 is driven against plate 23 thereby forcing it into abutment with the cap end wall 18 and forcing post 24 into a position protruding through passage 19. Movement of the post urges it against the hinged flap 20 causing the flap to assume an upright position as shown in FIG. 4.

Once the syringe has been replaced in the case and the case capped, it is easily recognized as having been used, and possibly contaminated, by virtue of the post bearing a medical waste symbol 34 extending through the end wall 18 of the cap. The cap 11 is now retained in its locked position by the rim annular ridge 31 now being snap fitted into the end cap annular indentation 17. The abutment of the plate 23 with the end wall 18 and the close fit of the post 24 through passage 19 serves to seal the passage.

Alternatively, the aperture 31 may be oriented longitudinally in the end of the tubular member solid portion 26. However, a transverse orientation is much preferred so that an exposed needle need never be pointed towards an operator's hand during sheathing. It should also be understood that plate 23 may be designed so as to be driven by the end of the syringe plunger 42 rather than by the end of the tubular member 25 during recapping.

From the foregoing it is seen that a syringe case is now provided which overcomes problems long associated with sheathing and housing syringes. It should however be understood that the just described embodiment merely illustrates principles of the invention in its preferred form. Many modifications, additions and deletions may, in addition to those expressly recited, be made thereto without departure from the spirit and scope of the invention as set forth in the following claims.

What is claimed is:

1. A case for housing a syringe of the type having an elongated barrel with a hub at one end from which a needle extends and a protective sheath removably mounted to the hub covering the needle, and wherein the case comprises an elongated, tubular member open at one end and having an aperture located adjacent the other end extending completely through said tubular member, said aperture being oriented transversely with respect to the axis of said elongated tubular member and being sized and shaped to receive and releasably hold the protective sheath, and means for removably capping said tubular member open end, whereby the needle may be manually unsheathed by a user for syringe use and resheathed by the user for syringe storage by insertion of the sheath into and extraction from the aperture.

2. The case of claim 1 wherein said aperture extends completely through an end portion of said tubular member.

3. The case of claim 1 wherein said means for capping comprises a cap having repositionable indicator means for indicating that said cap has been removed and replaced upon said tubular member.

4. The case of claim 3 wherein said indicator means comprises a plate movably mounted within said cap from which a post extends, and wherein said cap has a passage through which said post may extend.

5. The case of claim 4 wherein said cap further includes a movable flap for sealing said passage.

6. A case for housing a syringe having a needle, a hub from which the needle extends, a barrel coupled with the hub and a removable protective sheath covering the needle, wherein said case comprises an elongated tubular member having an open end and an aperture located adjacent the other end having a size and shape to hold the removable protective sheath, a cap for capping said open end of said tubular member and having a passage therethrough, and indicator means for indicating that said cap has been removed and replaced upon said tubular member, said indicator means including a post mounted adjacent said tubular member open end positioned to extend through said cap passage upon said cap being replaced on said tubular member.

7. The case of claim 6 wherein said aperture is oriented transversely with respect to the axis of said elongated tubular member.

* * * * *